United States Patent
Tu et al.

(10) Patent No.: US 11,439,573 B2
(45) Date of Patent: Sep. 13, 2022

(54) PHOTOPOLYMERIZABLE BASE COAT FOR A NAIL

(71) Applicant: Coty Inc., New York, NY (US)

(72) Inventors: Xiaoyan Tu, Valencia, CA (US);
Justina Vy Lan Hoang, El Segundo, CA (US); Jay Jayasingha Kingsley, Reseda, CA (US)

(73) Assignee: Wella Operations US LLC, Calabasas, CA (US)

( * ) Notice: Subject to any disclaimer, the term of this patent is extended or adjusted under 35 U.S.C. 154(b) by 489 days.

(21) Appl. No.: 16/349,509

(22) PCT Filed: Dec. 15, 2017

(86) PCT No.: PCT/US2017/066790
§ 371 (c)(1),
(2) Date: May 13, 2019

(87) PCT Pub. No.: WO2018/118707
PCT Pub. Date: Jun. 28, 2018

(65) Prior Publication Data
US 2019/0336422 A1    Nov. 7, 2019

Related U.S. Application Data

(60) Provisional application No. 62/438,112, filed on Dec. 22, 2016.

(51) Int. Cl.
*A61K 8/35* (2006.01)
*A61K 8/73* (2006.01)
*A61K 8/81* (2006.01)
*A61Q 3/02* (2006.01)

(52) U.S. Cl.
CPC ............... *A61K 8/35* (2013.01); *A61K 8/731* (2013.01); *A61K 8/8152* (2013.01); *A61Q 3/02* (2013.01); *A61K 2800/594* (2013.01); *A61K 2800/5922* (2013.01); *A61K 2800/81* (2013.01); *A61K 2800/95* (2013.01)

(58) Field of Classification Search
None
See application file for complete search history.

(56) References Cited

U.S. PATENT DOCUMENTS

| 9,050,272 B1 * | 6/2015 | Homma | A61K 8/731 |
| 2015/0328104 A1 | 11/2015 | Kergosien | |
| 2017/0056313 A1 * | 3/2017 | Valia | A61K 8/37 |

FOREIGN PATENT DOCUMENTS

WO    WO-2011011304 A2    1/2011

OTHER PUBLICATIONS

Beth Livesay. "Hard Vs. Soft: A Closer Look at Gels" Nails, <https://www.nailsmag.com/383698/hard-vs-soft-a-closer-look-at-gels> available Aug. 4, 2014, accessed Nov. 3, 2021 (Year: 2014).*
"International Application Serial No. PCT/US2017/066790, International Search Report dated Mar. 21, 2018", 6 pgs.
"International Application Serial No. PCT/US2017/066790, Written Opinion dated Mar. 21, 2018", 8 pgs.
"PECOREZ AC-50 Material Safety Data Sheet", [Online] Retrieved from the Internet: <http://www.phoenix-chem.com/ESW/Files/ MSDS-PECOREZ-AC-50-2010.pdf>, (Jan. 4, 2010).
Gottschalck, T E, et al., "International Cosmetic Ingredient Dictionary and Handbook, Acrylates/c10-30 Alkyl Acrylate Crosspolymer; Acrylates Copolymer", International Cosmetic Ingredient Dictionary and Handbook, the Cosmetic, Toiletry, and Fragrance Association, Washington, D.C., USA, (Jan. 1, 2008), 46-47.

* cited by examiner

*Primary Examiner* — Nicole P Babson
(74) *Attorney, Agent, or Firm* — Dennemeyer & Associates LLC; Victoria Friedman; Anita Cepuritis

(57) ABSTRACT

A photopolymerizable composition suitable for forming a polymerized base coat of a substantially uniform mixture of nitrocellulose and crosslinked (meth)acrylate polymer is disclosed. The composition comprises an ethyl acetate solution including multiple (meth)acrylate monomers, nitrocellulose, a rapid release copolymer of alkyl acrylate monomers, a chain extended di-(hydroxyethylmethacryloyl) trimethylhexyl dicarbamate oligomer of weight average molecular weight of 10 to 20 kDa, one or more plasticizers and a photoinitiator.

11 Claims, No Drawings

PHOTOPOLYMERIZABLE BASE COAT FOR A NAIL

PRIORITY

This application is a U.S. National Stage Filing under 35 U.S.C. 371 from International Application No. PCT/US2017/066790, filed on Dec. 15, 2017, and published as WO 2018/118707 on Jun. 28, 2018, which application claims the benefit of priority from U.S. Provisional Patent Application Ser. No. 62/438,112, filed on Dec. 22, 2016, which are herein incorporated by reference in their entirety.

BACKGROUND

Commercial gel nail base coats typically include a base coat, a color coat and a top coat. Recent developments in the technology combine pre-existing film forming polymers such as cellulose acetate butyrate with photopolymerizable gels based upon (meth)acrylate technology. The gels include crosslinkers that contribute hardness, resistance to dissolution, resistance to scratching and long wear yet in combination with film formers contribute flexibility. Nail salons are the typical commercial establishments handling this work because it entails careful application and curing by UV radiation.

Photopolymerizable (meth)acrylate coats find significant applications in diverse commercial fields including not only nail base coats but also as paints and coats for automobiles, commercial vehicles, trains, appliances, and metal structures such as steel fabrications. The monomeric components of coats not only are polymerized into long carbon chains by photolytic action but are also crosslinked with carbon chains between these chains through the use of di, tri and tetra (meth)acrylate oligomers. Strength of the crosslinked or photopolymerized compositions is also increased by use of urethane (carbamate) chains within the three dimensional structure of the polymerized composition. The result of extensive crosslinking of these compositions produces coats that are impervious to all manner of attack including scratching, chipping, organic solvents, abrasives and ordinary environmental activity. These qualities are benefits for most fields because they provide permanent, impervious, non-removable, strong but flexible protective coats for metals and other substrates that would otherwise be susceptible to environmental degradation.

Because these same coats are used for nail base coats, these beneficial attributes for other commercial fields such as auto polymer coats become problematic for nail polymer coats. A nail polymer coat should be removable. However, a nail polymer coat that mimics the ingredients, concentrations and extent of crosslinking of auto polymer coats, would be highly undesirable. Once applied, it could not be removed from a nail. Growth of the nail would be the only practical but unsightly manner of removal of such a polymer coat.

In addition, a base polymer coat should adhere to the proteinaceous material of the human nail. This substrate entirely differs in chemical make-up from the steel and aluminum of vehicles and appliances. Adhesion cannot be achieved by covalent bonding which would practically eliminate easy removal. Adhesion also cannot be achieved by electrostatic interaction as this interaction also would eliminate easy removal.

To solve these problems, nail polymer coat manufacturers have lowered the degree of crosslinking, employed additional components to soften the photopolymerized or cured coat and incorporated solvent-soluble film formers to enable solvent removal. The patent literature describes attempts to provide a cured base coat that is both tough, flexible, scratch and abrasion resistant yet can be easily removed by soaking the cured or photopolymerized coat in organic solvent.

However, these cured compositions are interpenetrating networks of mutually incompatible polymeric materials so that substantially homogeneous coats are not produced. Instead, these coats have a continuous phase of one polymeric material in which is dispersed separate discontinuous domains of the second polymer. This second polymer is readily soluble in organic solvent. This construction enables ready removability by organic solvents but also lessens the strength, toughness and adherence of the cured base coat. The discontinuous domains of second polymer also make the coating susceptible to residue remains attached to the nail plate, sometimes stubbornly. The discontinuous domains also make the base coat susceptible to undesirable detachment from the nail substrate under usual wear conditions. Therefore, there is a need to develop nail base coats that are both readily removable while demonstrating the strength, adherence and toughness of cured nail base coats.

SUMMARY

The present invention is directed to a photopolymerizable nail base coat, to the corresponding photopolymerized nail base coat, a method of application and curing the photopolymerizable nail base coat and a nail with a photopolymerized nail base coat.

Compositional aspects of the photopolymerizable nail base coat include (meth)acrylate monomers, a di(meth)acrylate oligomer, a rapid release polymer of alkyl acrylates, nitrocellulose, plasticizers and a photoinitiator, all in solution with one or more solvents such as ethyl acetate alone or in combination with minor amounts of one or more alkanols. The di(meth)acrylate oligomer is a moderately high weight average molecular weight oligomer. The monomers include hydroxyethyl and hydroxypropyl esters of methacrylic acid, and isobornyl (meth)acrylate. A minor amount of acrylic acid is also included. The compositional aspects of the photopolymerizable coat also include a phosphine oxide, a phosphinate and phenone photoinitiators and surfactants, as well as optional oxidation and spontaneous polymerization inhibitors.

The photopolymerizable nail base coat is formulated as a single, essentially homogeneous mixture of the components of the composition constituting the photopolymerizable nail base coat. It is stable for a period of time and if the components separate, it can be easily shaken to recombine the phase separation of solvent and gel components of the photopolymerizable nail base coat.

The photopolymerized nail base coat is produced by use of UV radiation also known as actinic radiation for a period of time sufficient to photopolymerize the monomeric components and at the same time to cross link the oligomer with the monomeric components of the photopolymerizable nail base coat. The oligomer component enables long cross links which in part contribute to the physical macromolecular construct of the photopolymerized nail base coat. In addition, the nitrocellulose is miscible in the photopolymerized (meth)acrylate network so that a substantial to essential uniform mixture of these two network components is produced.

Application of the photopolymerizable nail base coat is accomplished by brush, spray, drip or similar application technique. A portion of the photopolymerizable nail base coat is applied to the nail or appropriate part of the nail. The photopolymerizable coat is exposed to UV radiation to cause curing. The typical photopolymerized nail base coat is a clear gel base coat over which is usually applied a color coat and a clear top coat.

DETAILED DESCRIPTION

The present invention is directed to a photopolymerizable nail base coat that preferably is a substantially homogenous liquid composition that can be photopolymerized to produce a substantially homogeneous solid mixture or substantially homogeneous solid solution of polymerized, crosslinked (meth)acrylate components and nitrocellulose. The photopolymerized nail base coat is an interpenetrating network of the crosslinked (meth)acrylate components and nitrocellulose. The interpenetrating network is phase miscible rather than phase separate.

Definitions

Unless defined otherwise, all technical and scientific terms used herein have the same meaning as commonly understood by a person of ordinary skill in the art.

As used in the specification and the appended claims, the singular forms "a," "an" and "the" include plural referents unless the context clearly dictates otherwise.

The term "may" in the context of this application means "is permitted to" or "is able to" and is a synonym for the term "can." The term "may" as used herein does not mean possibility or chance.

The (meth)acrylate monomers are acrylate and (meth) acrylate ester compounds wherein the esterifying alcohol is an aliphatic mono-alcohol or an aliphatic diol. The aliphatic group preferably is an alkylene group of two or three carbons or is a cycloalkyl, heterocycloalkyl or bicycloalkyl group of six to ten carbons such as cyclohexyl or norbornyl or tetrahydrofuran. The parenthesis surrounding the prefix "meth" means that the term (meth)acrylate encompasses methacrylic acid and acrylic acid compounds. Without a parenthesis, the term methacrylate means only the methacrylate esters, and does not include acrylic esters. The suffix "ate" means that the term (meth)acrylate is an ester formed by combination of a monoalcohol or diol with methacrylic acid or acrylic acid. Preferred (meth)acrylates include hydroxyethyl (meth)acrylate, hydroxypropyl (meth)acrylate and isobornyl (meth)acrylate. The preferred (meth)acrylate is any of the methacrylates.

The crosslinker di(meth)acrylate is a chain extended or non-extended straight chain oligomer having (meth)acrylate moieties at both ends of the oligomer. The backbone of the oligomer between the two (meth)acrylate end groups may be any one of several backbones, including polyols such as polyethylene glycol, polypropylene glycol, polybutylene glycol, diurethane (i.e., dicarbamate) glycols formed by combination of a diol and a diisocyanate so as to form a central diol moiety coupled to a diisocyanate at each terminal hydroxyl of the diol and a diol coupled to the other terminus of the diisocyanate so as to form a diol-carbamate-diol-carbamate-diol moiety. The terminal hydroxyls of this backbone form the ester groups with the (meth)acrylate termini. The chain length of the dicarbamate glycol backbone can be extended or shortened by the number and length of the diols and diisocyanates used. Alternatively, polyol and diisocyanate roles of this backbone can be reversed so that the termini of the intermediate are isocyanate groups, e.g., an excess of diisocyanate is coupled with the polyol so that the backbone intermediate ends with the isocyanate moiety of the diisocyanate (the other end of the diisocyanate being combined with the hydroxyl of the polyol to form the carbamate group). In this backbone reversal, the isocyanate termini of the backbone intermediate are coupled with the hydroxyl of an hydroxyalkyl (meth)acrylate to form the oligomer. In addition and as a further alternative, the diisocyanate can be the central moiety, each end of which is coupled to an hydroxyl of the hydroxyalkyl (meth)acrylate moiety.

The (meth)acrylate monomers are liquids and are reactive polymerization components of the photopolymerizable nail base coat. Because of the hydrophobic character of the bulky isobornyl group of the isobornyl (meth)acrylate adhesion of the base coat to the hydrophobic apolar residues of the keratin fibrous structure of the nail plate is enhanced. However, hydrophobic enhancement is coupled with the hydrophilic adhesion promoted by the hydroxyl containing (meth)acrylates and the primary amide structure of the same keratin fibers. The balance of the hydrophilic and hydrophobic interaction enables significant adherence between the base coat of the invention and human nail plate.

The molecular weight of a polymer or oligomer used according to the invention may be measured by a weight average molecular weight, and the distribution of molecules of different molecular weights of a polymer or oligomer used according to the invention is determined by its polydispersity index. Molecular weight is expressed as Daltons (Da) and kiloDaltons (kDa). The acronym wmw stands for weight average molecular weight Polydispersity is a unit-less number and indicates the breadth of the Gaussian curve plotted as the molecular weight of individual molecules (X axis) against the number of molecules at each molecular weight (Y-axis).

The terms "photopolymerizable" and "photopolymerized" are understood to mean respectively a polymerizable mixture of ingredients and a polymerized material. Synonyms for photopolymerizable and photopolymerized are curable and cured or polymerizable and polymerized. A polymerized (meth)acrylate composition is also known as a photopolymerized (meth)acrylate composition or a cured (meth)acrylate composition.

The terms "sol" and "gel" are understood to mean liquid and solid portions of a polymerizing composition. An unpolymerized mixture of monomers and a crosslinker is typically a low viscosity, fluid liquid. This is the sol stage of the mixture. As polymerization proceeds, the monomers polymerize to become long linear chains. If no crosslinker is present, the result of this polymerization is a thermoplastic polymer. If a crosslinker is present, it links the individual chains together to form a three dimensional net or network. With either of these polymerization processes, the growing polymer becomes solid. The solid fraction of the polymerizing composition is the gel stage. At the beginning of the polymerization, the sol is a continuous phase and the gel is miniscule and is a discontinuous phase. As polymerization proceeds, the concentration of sol lessens and the concentration of gel increases. The point of polymerization where the gel becomes the continuous phase and the sol is the discontinuous phase polymers extend in length is the gelation point. With thermoplastic polymerization, the gel point occurs late in the polymerization. With thermoset polymerization where a moderate to high amount of crosslinker is present, the gel point occurs early in the polymerization. Typical gel points for thermoset polymers occur at a moderately retarded time when at least 3 to 5 weight percent of crosslinker is present and occur moderately early when at least 15 weight percent of crosslinker is present.

The term "about" is understood to mean 10 percent of the recited number, numbers or range of numbers.

The term "about 0 wt %" is understood to mean that no substance, compound or material to which zero (0) refers is present, up to a negligible but detectable amount is present, assuming that the detectability can be determined on a parts per million basis.

The term "non-solvent" is understood to mean no organic liquid solvent such as ethyl acetate, methyl ethyl ketone, acetone, mono alcohols such as methanol, ethanol, propanol or butanol, or any other organic solvent having an STP boiling point of 100° C. or lower and in which (meth) acrylate monomers and oligomers and nitrocellulose will dissolve.

The term "non-hydrogen bonding" is understood to mean a compound or group that does not contain a hydroxyl group and that can form molecule to molecule interaction through hydrophobic or lipophilic interaction.

In addition, where features or aspects of the invention are described in terms of Markush groups, those skilled in the art will recognize that the invention is also thereby described in terms of any individual member or subgroup of members of the Markush group. For example, if X is described as selected from the group consisting of methyl, ethyl or propyl, claims for X being methyl and claims for X being methyl and ethyl are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

The Photopolymerizable Nail Base Coat

The photopolymerizable nail base coat is formed with a composition of multiple (meth)acrylate monomers, nitrocellulose, a rapid release copolymer of alkyl acrylates, a (meth)acrylate crosslinker and one or more solvents such as ethyl acetate alone or in combination with alkanols such as isopropanol or ethanol, preferably isopropanol. The preferred (meth)acrylate monomers and (meth)acrylate crosslinker are the methacrylate monomers and methacrylate crosslinker. Additional components of the composition include a photoinitiator such as a phosphine oxide, a phosphinate and a phenone, an oxidation inhibitor and surfactant. The photopolymerizable nail base coat is a substantially homogeneous liquid mixture of these components.

The (meth)acrylate crosslinker includes a di(meth)acrylate oligomer or chain extended di(meth)acrylate oligomer of moderate weight average molecular weight and a moderate to moderately broad polydispersity. The weight average molecular weight of the chain extended crosslinker is in the range of 2 kDa to 20 kDa, preferably in the range of 5 kDa to 20 kDa, more preferably about 10 kDa to about 20 kDa, most preferably about 13 kDa to about 17 kDa with a polydispersity of 1.0 to 5.0, preferably about 2.0 to 5.0.

Another preferred wmw of the chain extended crosslinker is about 14 kDa to about 16 kDa and especially about 15 kDa with a polydispersity of about 2.0 to about 4.0. The weight average molecular weight of the di(meth)acrylate oligomer without chain extension is in the range of 400 to 600 Da (0.4 kDa to about 0.6 kDa), preferably about 460 to about 480 Da with a polydispersity of about 1 to 1.1.

The crosslinker aspect of the invention can encompass a chain extended di(meth)acrylate crosslinker I having the foregoing weight average molecular weight and polydispersity characteristics and having either a polyol or a polyol-carbamate backbone. An example of such a chain extended crosslinker includes one formed with a polyol, trimethylhexyl diisocyanate and methacrylic acid. The preferred polyol is ethylene glycol or a polymer thereof. The variation of weight average molecular weight for establishing the moderate weight average molecular weights can be accomplished by increasing the length of the backbone. Formation of multiple backbone units of the combination of a multiple number (n) of diisocyanates (Y groups) and multiple number+1 (n+1) of ethylene glycols, propylene glycols, polypropylene glycols or polyethylene glycols (X group) enables this backbone intermediate variation. For example, combination of two Y groups and three X groups produces HO—X—Y—X—Y—X—OH as the hydroxyl terminated backbone. Variation can also be accomplished by use of a higher weight average molecular weight polyol, such as polyethylene glycol, for the middle X groups of the foregoing example and use of ethylene glycol for the terminal X groups. Ester capping the hydroxyl termini of the backbone intermediate with methacrylic acid forms the di(meth)acrylate crosslinker. Variation can also be accomplished through use of the polyol combined as an ester with the methacrylic acid and exclusion of the diisocyanate.

Another version of the chain extended crosslinker having the foregoing weight average molecular weight and polydispersity parameters is chain extended crosslinker II which encompasses a backbone intermediate of one or more polyols (i.e. an m number of polyols) with m+1 diisocyanates (Y) so as to provide the backbone intermediate with isocyanate termini of the formula Y—(X)$_m$—(Y—X)$_l$—Y wherein l is zero or 1. This is the reverse of the backbone intermediate for chain extended crosslinker I. Extended crosslinker I backbone intermediate is terminated by hydroxyls while extended crosslinker II backbone intermediate is terminated by isocyanates. These isocyanate termini are combined with the hydroxyl of an hydroxyalkyl (meth)acrylate to form the chain extended crosslinker II of the formula (meth)acryloyl-O-alkylenyl-O—Y—(X)$_m$—(Y—X)$_l$—Y—O-alkylenyl-O-(meth)acryloyl wherein the alkylenyl group can be a multimethylenyl group of 2 to 6 carbons, preferably 2 or 3 carbons, more preferably 2 carbons. The Y—O bonding group and the Y—X bonding group in this formula are the carbamate group —N—C(=O)—O—.

Preferred polyols for the chain extended crosslinker I and chain extended crosslinker II are polyethylene glycol and polypropylene glycol containing from 2 to 500 glycol units, preferably from 5 to 400 glycol units, more preferably from 10 to 250 glycol units, most preferably from 100 to 250 glycol units. An especially preferred number of glycol units is the number that will provide a chain extended crosslinker oligomer of weight average molecular weight of about 10 kDa to about 20 kDa, preferably about 12 kDa to about 18 kDa, more preferably about 13 kDa to about 17 kDa. The preferable diisocyanate and methacrylate for inclusion with such preferred numbers of glycol units are trimethylhexyl diisocyanate and hydroxyethyl methacrylate.

Preferred diisocyanates include trimethylhexyl diisocyanate, isophorone diisocyanate, methylene bis (4-cyclohexylisocyanate), hexamethylene diisocyanate and similar aliphatic diisocyanates.

Another alternative as the oligomeric crosslinker is the di(meth)acrylate oligomer without a chain extension. This oligomer is the combination of a diisocyanate and a hydroxyalkyl (meth)acrylate without inclusion of a polyol. This oligomer has the formula (meth)acryloyl-O-alkylenyl-O—Y—O-alkylenyl-O-(meth)acryloyl wherein the alkylenyl group can be ethylenyl, propylenyl or butylenyl and the Y—O bonding group is the carbamate group. The combination of hydroxyethyl (meth)acrylate and trimethylhexyl diisocyanate provides an example of this oligomer. When the (meth)acrylate is hydroxyethyl methacrylate, this oligomer has the formula $CH_2=C(CH_3)-C(=O)O-(CH_2)_2-OC(=O)NH-(CH_2)_2CH(CH_3)C(CH_3)_2CH_2-NH-C(=O)O-(CH_2)_2-OC(=O)-C(CH_3)C=CH_2$. Because on a commercial basis the trimethylhexyl diisocyanate can contain impurities of a dimethylhexyl diisocyanate as well as a trimethylpentyl diisocyanate while the hydroxyethyl methacrylate can contain impurities of hydroxy propyl methacrylate as well as the corresponding acrylate esters, the molecular weight of this oligomer group can be a weight average molecular weight instead of a molecular weight of a single molecule.

The moderate wmw and high polydispersity of the chain extended crosslinker in combination with solvent is believed to facilitate effective cross linking as the polymerizing composition reaches and passes the gel point. The solvent characteristics and the polydispersity of the crosslinker help promote molecular translation during the polymerization process and in particular when the increasing viscosity and gel stage tend to retard and/or inhibit molecular movement or kinetic translation.

The monomer aspect of the invention encompasses (meth)acrylate ester monomers that display a balance of hydrogen bonding and hydrophobic bonding so as to facilitate adherence to the nail plate substrate. This balance is managed by incorporation of a (meth)acrylate ester that displays hydrophobic interaction through a bulky, lipophilic group, the isobornyl group. The ratio of hydrogen bonding to hydrophobic bonding (meth)acrylate esters facilitates this balance.

While it is not a parameter of the invention, it is believed that the inclusion of the hydrophobic bonding (meth)acrylate facilitates interaction and adherence with the hydrophobic pendent groups of the keratin protein of the nail plate. Because the nail plate also presents a hydrophilic structure through its primary sequence (the amide bonds), a balance with hydrogen bonding achieves a dual interaction. The dual interaction ameliorates or otherwise lessens the repulsion of (meth)acrylate hydrogen bonding groups by the hydrophobic groups of the keratin and of (meth)acrylate hydrophobic groups by the hydrophilic primary structure of the keratin.

The (meth)acrylate esters displaying hydrogen bonding properties include hydroxyethyl (meth)acrylate and hydroxypropyl (meth)acrylate. In part because of their liquid character at ambient temperature, the hydrogen bonding (meth)acrylate esters contribute to the solubilizing and fluidity aspects of the photopolymerizable nail base coat. The preferred (meth)acrylate monomers are the methacrylate monomers.

Nitrocellulose is a component of the compositional aspect of the photopolymerizable nail base coat of the invention. Nitrocellulose is soluble in the (meth)acrylate monomers and di(meth)acrylate crosslinker of this composition. Nitrocellulose is also miscible in the polymerized network of the monomers and crosslinker so that the photopolymerized (cured) nail base coat constitutes a substantially homogeneous polymeric network.

Nitrocellulose is commercially available as different grades of nitrated hydroxyls of the beta glucose monomeric unit of cellulose. Because of the explosive character of highly nitrated cellulose, it is dampened with solvent such as water, ethanol or isopropanol. The lower nitrogen content nitrocelluloses remain highly flammable but are not regarded as highly explosive. These lower nitrogen content grades serve as appropriate film formers for the present invention. These have a weight percent of nitrogen relative to the total weight of the nitrocellulose in a range of about 10 wt % to about 12.3 wt %. Preferably, the weight percent of nitrogen is about 10.7 to about 12.3 wt %, more preferably about 11.7 wt % to about 12.2 wt %.

It is commonplace to obtain the nitrocellulose dampened with water or preferably ethanol or isopropanol. A nitrocellulose supply dampened in ethyl acetate can readily obtained. Alternatively, nitrocellulose dampened with ethyl acetate can be prepared by multiple washing the water or ethanol dampened nitrocellulose with ethyl acetate to exchange the original dampening agent for ethyl acetate.

Nitrocellulose is a film former product and is soluble in aliphatic alcohols and aliphatic esters and specifically is soluble in ethyl acetate. However, because nitrocellulose is similar in structure and polarity to cellulose acetate and cellulose acetate butyrate and these film formers are not miscible in crosslinked (meth)acrylate polymer, it can be anticipated that nitrocellulose would also not be miscible with crosslinked (meth)acrylate polymer. Nevertheless, it has been discovered that by adjusting the concentration ratio of hydrogen bonding and hydrophobic monomers as well as the concentration of the di(meth)acrylate crosslinker, nitrocellulose having a low nitrogen content is substantially to fully miscible with the crosslinked polymer aspect of the photopolymerized nail base coat.

The rapid release copolymer is a pre-formed, linear acrylate copolymer of a substantial molar amount of butyl acrylate and a lesser molar amount of a mixture of alkyl acrylates wherein the alkyl group ranges from C1 to C3 alkyls, preferably methyl and ethyl, more preferably methyl. The molar ratio of butyl acrylate to the alkyl acrylate mixture is in the range of about 2:1 to about 1:2; preferably about 1:0.8 to about 1:1.5; more preferably about 1:1 to about 1:1.2 with the first number of the ratio being butyl acrylate and the second number being the alkyl acrylate mixture. The weight average molecular weight of the rapid release copolymer is in a range of from about 3 kDa to about 20 kDa, preferably about 4 kDa to about 15 kDa, more preferably about 4 kDa to about 10 kDa, most preferably about 5 kDa. The polydispersity of the rapid release copolymer across all weight average molecular weight ranges is from about 1.3 to about 2.0, preferably about 1.5 to about 1.8. The rapid release copolymer is not crosslinked. Rather it is a linear, thermoplastic acrylate copolymer The monomer concentrations of the compositional aspect of the photopolymerizable nail base coat on a weight percentage basis relative to the total weight of the photopolymerizable composition (including the solvents such as ethyl acetate alone or in combination with alkanol) ranges from: about 5.0 wt % to about 30.0 wt %, preferably 9.0 wt % to about 20 wt %, especially preferably about 10.0 wt % to about 18 wt %, more preferably about 10.0 wt % to about 15.0 wt %, especially more preferably about 10.0 wt % to about 14 wt %, most preferably about 10.5 wt % to about 13 wt %, and especially most preferably about 10.6 wt % to about 12.8 wt %.

The individual monomer concentrations relative to the total weight of the polymerizable composition have the following ranges:

A) Hydrogen bonding (meth)acrylates—about 4 wt % to about 29.0 wt %, preferably 8.0 wt % to about 19.0 wt %, especially preferably about 8.0 wt % to about 14 wt %, more preferably about 8.0 wt % to about 12.0 wt %, most preferably about 8.4 wt % to about 10.0 wt %;

B) Hydrophobic (meth)acrylates—about 2.0 wt % to about 6.0 wt %, preferably about 2.0 wt % to about 4.5 wt %, especially preferably about 2.0 wt % to about 3.5 wt %, more preferably about 2.2 wt % to about 2.8 wt %.

C) Preferred (meth)acrylates of the hydrogen bonding and hydrophobic categories are the methacrylates.

Preferred (meth)acrylate monomers and their concentrations in the polymerizable composition (with about 50 wt % ethyl acetate) include:

1) hydroxypropyl (meth)acrylate—about 5.0 wt % to about 15 wt %, preferably about 5.0 wt % to about 8.5 wt %, especially preferably about 5.8 wt % to about 6.8 wt %;
2) hydroxyethyl (meth)acrylate—about 2.0 wt % to about 10 wt %, preferably about 2.0 wt % to about 5.0 wt %, especially preferably about 2.6 wt % to about 3.2 wt %;
3) acrylic acid—about 0.1 wt % to about 1.0 wt %, preferably about 0.1 wt % to about 0.9 wt %;
4) isobornyl (meth)acrylate—about 2.0 wt % to about 4.0 wt %, preferably about 2.2 wt % to about 2.8 wt %.
5) Preferred specific (meth)acrylate monomers are the specific methacrylate monomers.

The concentration of the crosslinker falls within the following weight percentage range relative to the total weight of the composition: about 5.0 wt % to about 30.0 wt %, preferably about 11.0 wt % to about 16 wt %, especially preferably about 12 wt % to about 14 wt %, more preferably about 13 wt %.

The concentration of nitrocellulose in weight percentage relative to the total weight of the polymerizable composition is in a range of from about 2.0 wt % to about 20.0 wt %, preferably about 5 wt % to about 14 wt %, especially preferably 5 wt % to about 12 wt %, more preferably about 5 wt % to about 8 wt %, most preferably about 7 wt %.

The concentration of rapid release copolymer of alkyl acrylates is in a range of about 2.0 wt % to about 30 wt %, preferably about 4.0 wt % to about 7.5 wt %, especially preferably 4.5 wt % to about 5.5 wt %, more preferably about 5.1 wt % relative to the total weight of the polymerizable composition.

The concentration of plasticizer relative to the total weight of the polymerizable composition is in a range of about 3 wt % to about 6 wt %, preferably about 4 wt %. The preferred plasticizers include camphor and trimethyl pentanyl diisobutyrate at concentrations relative to the total weight of the polymerizable composition of about 1 wt % to about 3 wt %, preferably about 1 wt % to about 2 wt %, more preferably about 1.6 wt % to about 1.7 wt % for camphor and about 2 wt % to 4 wt %, preferably about 3 wt % to about 4 wt %, more preferably about 3.3 wt % to about 3.4 wt % for trimethyl pentanyl diisobutyrate.

Any suitable photoinitiator or combination may be combined with the other components of the photopolymerizable nail base coat to enable photopolymerization. Phosphine oxide and/or phosphinate photoinitators can be employed alone or in combination with benzophenone derivatives as well as with benzil ketals, alpha hydroxyl alkyl phenones and acetophenone derivatives. The phosphine oxides are commercially available and described in the literature. See U.S. Pat. Nos. 4,298,738, 4,737,592 and 6,298,738 and Irgacure® and Lucirin® brands of phenones and phosphine oxides. One particular phosphine oxide photoinitiator useful for inclusion in the photopolymerizable nail base coat is ethyl-2,4,6-trimethylbenzoyl phenylphosphinate. Another is 2,4,6-trimethylbenzoyldiphenylphosphine oxide (TPO). Yet another is bis-(trimethylbenzoyl)phenylphosphine oxide. Another is hydroxycyclohexyl phenyl ketone, as well as benzyl dimethyl ketal. A typical concentration of the photoinitiator may range from 0.1 wt % to 20 wt %, preferably about 0.1 wt % to about 10 wt %, more preferably about 0.2 wt % to about 5 wt % relative to the total weight of the composition.

The solvent, ethyl acetate alone or in combination with low molecular weight, high volatility alkanols such as ethanol or isopropanol, is present in the photopolymerizable composition at a concentration of about 30 wt % to about 70 wt %, preferably 40 wt % to 60 wt %, more preferably about 50 wt % to about 54 wt %, most preferably about 50.5 wt % to about 54 wt %, especially most preferably about 53.7 wt %. A preferably low molecular weight, high volatility alkanol is isopropanol.

Inclusion of one or more polymerization regulators and anti-oxidation agents may also be desirable. These include hydroquinones and ascorbic acid derivatives. These regulators and agents may range in concentration from 0.0001 wt % to about 5 wt %.

Inorganic pigments and dyes such as ferric oxide; FD&C red 4, 6, 7, 17, 21, 22, 27, 28 or 33; FD&C yellow 5 or 6; D&C violet 2, 3 or 4; titanium oxide; D&C orange 4, 5 or 10; FD&C green 3, 5 or 6, and similar colorants are optional, are typically not present in the base coat but may be incorporated if desired. Suitable concentrations range from 0.01 wt % to 0.05 wt %.

The Photopolymerized Nail Coat

Upon photopolymerization of the photopolymerizable composition, the (meth)acrylate monomers and di(meth)acrylate crosslinker polymerize to form a thermoset poly (meth)acrylate three-dimensional network. The solvent, ethyl acetate, is evaporated during this polymerization through the development of heat from the exothermic polymerization and typically from the heat generated by the UV apparatus used to cause polymerization. As the solvent such as ethyl acetate alone or with alkanols evaporates, the viscosity of the polymerizing composition increases because of the increased concentration of the remaining components and because the polymerizing (meth)acrylate components approach a gel stage. The hydrophobic (meth)acrylate and rapid release copolymer are believed to function as retardants of the onset of the gel stage so that polymerization and crosslinking may more effectively occur. As a result of the evaporation of the solvent and polymerization of the (meth)acrylate components, an interpenetrating network of the crosslinked (meth)acrylate polymer, the linear rapid release copolymer and the nitrocellulose is produced.

The concentration ranges of the components of the photopolymerized nail base coat are about double the concentration ranges of these components in the photopolymerizable composition. The doubling of the concentration ranges is produced by the removal by evaporation of the solvent. Because the concentration of solvent is about 50 wt % to about 55 wt %, its removal about doubles the concentrations of the remaining components.

In particular, the photopolymerized composition, a.k.a., a cured base coat for a nail, includes a crosslinked (meth)acrylate polymer of multiple (meth)acrylate monomers and di-(hydroxyethylmethacryloyl) trimethylhexyl dicarbamate oligomer. The di(meth)acrylate crosslinker oligomer has a weight average molecular weight preferably in the range of 5 kDa to 20 kDa. When the oligomer is not chain extended, its weight average molecular weight is in the range of 0.4 kDa to about 3 kDa, preferably about 0.4 kDa to about 0.5 kDa. When the oligomer is chain extended, its weight average molecular weight is preferably in the range of about 10 kDa to about 20 kDa, preferably 13 kDa to about 17 kDa with a high polydispersity. This high polydispersity means that the chain extended oligomer contains short chain molecules as well as long chain molecules. This combination is believed to facilitate molecular movement during the gel stage of curing because the gel viscosity is lowered relative to a viscosity of a composition containing primarily long chain molecules of crosslinker. The crosslinked (meth)acrylate polymer is in a mixture with nitrocellulose, the rapid release copolymer of alkyl acrylate monomers, one or more plasticizers and a photoinitiator. The monomers, oligomer, nitrocellulose, rapid release copolymer, plasticizers and photoinitiators are the same as described above for the photopolymerizable composition.

The weight percentages relative to the total weight of the photopolymerized composition (cured base coat) are for the multiple (meth)acrylate monomers: about 18.0 wt % to about 40.0 wt %, preferably about 20.0 wt % to about 36.0 wt %, more preferably about 21.0 wt % to about 30.0 wt %, especially more preferably about 22.0 wt % to about 28.0 wt %, most preferably about 24.0 wt % to about 26.0 wt %, especially most preferably about 24.0 wt % to about 25.0 wt %. Preferred (meth)acrylate monomers of the photopolymerized composition are the methacrylate monomers.

For the of the dicarbamate oligomer (di(meth)acrylate oligomer, preferably the dimethacrylate oligomer with chain extension), the weight percentages are: about 22.0 wt % to about 32 wt %, preferably about 24.0 wt % to about 28.0 wt %, more preferably about 25.0 wt % to about 27.0 wt %, most preferably about 26 wt %.

For the nitrocellulose, the weight percentage is about 10.0 wt % to about 28.0 wt %, preferably about 12.0 wt % to about 24.0 wt %, more preferably about 13.0 wt % to about 15.0 wt %, most preferably about 14 wt % For the rapid release copolymer the weight percentage is about 8.0 wt % to about 15.0 wt %, preferably about 9.0 wt % to about 11.0 wt % %, more preferably about 9 wt % to about 11 wt %.

For the plasticizer, the weight percentage is about 8.0 wt % to about 12.0 wt %, preferably 9 wt % to about 11 wt %.

For the photoinitiator, the weight percentage is about 5 wt % to about 7 wt %.

The weight percentages of the (meth)acrylate monomers relative to the total weight of the photopolymerized composition are:
1) hydroxypropyl (meth)acrylate—about 10.0 wt % to about 17.0 wt %, preferably about 11.6 wt % to about 13.6 wt %;
2) hydroxyethyl (meth)acrylate—about 4.0 wt % to about 10.0 wt %, preferably about 5.2 wt % to about 6.4 wt %;
3) acrylic acid—about 0.2 wt 6 to about 2.0 wt %, preferably about 0.2 wt % to about 1.8 wt %;
4) isobornyl (meth)acrylate—about 4.0 wt % to about 8.0 wt %, preferably about 4.4 wt % to about 5.6 wt %.

5) Preferred specific (meth)acrylate monomers of the photopolymerized composition are the specific methacrylate monomers While it is not a limitation of the invention, it is believed that the photopolymerized nail base coat of an interpenetrating network of polymerized, crosslinked (meth)acrylate, rapid release copolymer and nitrocellulose is substantially homogeneous rather than separate phases of (meth)acrylate polymer, rapid release copolymer and nitrocellulose. In particular, it is believed that the three polymer networks including the crosslinked (meth)acrylate polymer, the linear rapid release copolymer and the nitrocellulose, constitute a mutually miscible interpenetrating network so that they form one solid phase rather than separate domains of crosslinked polymer, linear copolymer and nitrocellulose. It is believed that the balance of hydrophilic, hydrogen bonding groups and hydrophobic groups of the crosslinked (meth)acrylate polymer and the linear character of the rapid release copolymer promote and enable substantial to full miscibility of the nitrocellulose with these polymers. It is believed that this interaction contributes to the strength, toughness and flexibility of the photopolymerized nail base coat.

Nevertheless, in contrast to single phase crosslinked polymer nail coat, the photopolymerized nail base coat according to the invention is readily removable by soaking with organic solvent such as ethyl acetate, methyl ethyl ketone and/or ethyl alcohol or mixtures thereof. In particular, the photopolymerized nail base coat can be removed within 5 to 20 minutes of soaking. The photopolymerized base coat swells substantially uniformly so that the swelled coating can be easily and readily removed as a single piece or a few large pieces from the underlying nail plate. The swelling and removal preferably does not leave fragments of attached base coat. It is believed that the substantially uniform swelling phenomenon is due to the intimate, substantially homogeneous mixture of crosslinked (meth)acrylate polymer, the rapid release linear copolymer and nitrocellulose. The nitrocellulose and linear copolymer enable solvent access into and throughout the photopolymerized coat. The substantially homogeneous character of the photopolymerized coat enables solvent access to all parts of the coat rather than only to domains of film former as is described in the art.

The photopolymerizable nail base coat of the invention may be applied as a clear composition to a bare nail. The photopolymerizable nail base coat of the invention may optionally be combined with colorants and suspending agents to form a color base coat but coloration is not typical for the base coat composition.

Application of the photopolymerizable nail base coat of the invention is accomplished by ordinary salon techniques. Use of fine brushes, fine spray pencils and sponge wipers are typical applicators useful for applying the photopolymerizable nail base coat to nails and coated nails. Exposure to UV radiation produced with a UV light source at wave lengths of about 290 to 430 nm, preferably 300 to 420 nm will initiate polymerization. Times for exposure may range from 10 seconds to 10 minutes, preferably 15 second to 2 minute.

Multiple applications of the photopolymerizable nail base coat may also be employed especially if the nail plate is damaged and can be protected with a base coat. Fine tip brush work can be employed for this purpose. Following each application, the applied coat can be exposed to UV radiation.

Removal of the polymerized nail base coat may be accomplished by soaking in an organic solvent such as ethyl acetate, acetone, methyl ethyl ketone, ethanol or a mixture thereof for approximately 2 to 20 minutes, preferably 4 to 15 minutes, more preferably about 8 minutes. The soaking will substantially swell the entire base coat so that the swelled, loosened base coat may be lifted from the nail plate as a single piece or as a few large pieces and no or substantially no residual, small fragments remain attached or semi-attached to the nail plate.

EXAMPLES

In the following examples, the (meth)acrylate monomers and di(meth)acrylate crosslinker are the methacrylate monomers and di methacrylate crosslinker described above as preferred components. The curable gel blend is a mixture of the (meth)acrylate monomers, di(meth)acrylate crosslinker (Di-HEMA trimethylhexyldicarbamate chain extended oligomer) and photoinitiator and acrylic acid as described. The plasticizer mixture is a combination of camphor and trimethyl pentanyl diisobutyrate as described above.

TABLE 1

Examples 1 and 2

|  | Example 1 (Wt %) | Example 2 (Wt %) | Examples 3 |
|---|---|---|---|
| Nitrocellulose | 7.0 | 0.0 | Commercial gel polish basecoat |
| Plasticizer mixture | 5.0 | 5.0 | |
| Rapid Release Copolymer | 5.1 | 5.1 | |
| Curable gel blend | 28.7 | 28.7 | |
| Antioxidant | 0.5 | 0.5 | |
| Ethyl Acetate | 50.7 | 60.7 | |
| Colorant | 0.0025 | 0.0025 | |
| DCB Test-Failure Type | No failure | Cohesive Failure | Adhesive Failure |
| DCB Test-Fracture Energy (J/m$^2$) | NA | 1.7 | 2.8 |
| Removability Test (min) | 5.8 | NA | 7.6 |

All ingredients were mixed according to the percentages provided in Table 1.

DCB Test

A thin film of basecoat formulation was applied on a Vitro-Nails substrate to a 3 mil wet thickness. The film was cured under OPI LED lamp for 30 s. On top of the cured base coat, a 3-mil wet film of a commercial gel polish color coat was applied. A glass microscope slide was placed on top of the wet film and the assembly was cured under OPI LED lamp for 90 s. A Double Cantilever Beam (DCB) test was performed according to ASTM 3433 to the samples prepared from Example 1, Example 2 and Example 3. Formula with weak cohesive property exhibits failure through basecoat and the fracture energy can be measured in DCB test. Formula with weak adhesive property exhibit failure between the basecoat and Vitro-Nails and the fracture energy can be measured in DCB test. Formulas with strong cohesive and adhesive properties will have Vitro-Nails through color coat stay intact after test and failure occurs between color coat and glass substrate.

Example 1 does not exhibit cohesive or adhesive failure in DCB test. Example 2 exhibits cohesive failure through basecoat and the fracture energy is measured at 1.7 J/m$^2$. Example 3 exhibits adhesive failure between basecoat and Vitro-Nails substrate, and the fracture energy is measured at 2.8 J/m$^2$. The use of nitrocellulose in basecoat formulation significantly increases the adhesive and cohesive properties of the formula.

Removability Test

To evaluate the removability of the basecoat formulation, Example 1 is compared with a commercial gel polish basecoat formulation in Example 3. Both formulations were applied on a glass substrate to a 6 mil wet thickness and was cured and aged under OPI LED lamp for 5 minutes. On top of the cured basecoat, a 2-mil wet commercial gel polish topcoat was applied and cured under OPI LED lamp for 30 s. A lint-free wipe of 1×1 inches saturated with pure acetone was placed in the center of the cured topcoat. And the removal time was recorded when the cured film was swelled enough to lift up from the glass substrate. Example 1 removes 24% faster than the commercial basecoat formulation.

Statements of Embodiments of the Invention

The following statements of the embodiments of the invention (Statements 1-51) provide further characterization of the photopolymerizable composition, the photopolymerized composition, the photopolymerized base coat on a nail plate and methods for forming same.

1. A composition suitable for formation of a photopolymerized base coat on a nail, comprising: a mixture of components including multiple (meth)acrylate monomers, nitrocellulose, a rapid release copolymer of alkyl acrylate monomers, a di-(hydroxyethylmethacryloyl) trimethylhexyl dicarbamate chain extended oligomer of weight average molecular weight in the range of 10 kDa to 20 kDa, (urethane (meth)acrylate oligomer) one or more plasticizers and a photoinitiator wherein the mixture is in an ethyl acetate solution.

2. A composition according to statement 1 wherein the multiple (meth)acrylate monomers include hydroxyethyl (meth)acrylate, hydroxypropyl (meth)acrylate, isobornyl (meth)acrylate and acrylic acid.

3. A composition according to statement 1 wherein the plasticizers include camphor and trimethyl pentanyl diisobutyrate.

4. A composition according to statement 1 wherein the rapid release copolymer is a copolymer of butyl acrylate and a mixture of C1 to C3 alkyl acrylates.

5. A composition according to statement 4 wherein the rapid release copolymer has a weight average molecular weight range from 3 kDa to 20 kDa.

6. A composition according to statement 4 or 5 wherein the molar ratio of butyl acrylate to the mixture of alkyl acrylates ranges from 0.5:1 to 2:1.

7. A composition according to any one of statements 1-6 wherein the photoinitiator includes a phosphine oxide photoinitiator compound and hydroxycyclohexyl phenyl ketone.

8. A composition according to any one of statements 1-7 wherein the weight percentage ranges of components relative to the total weight of the composition are: about 5 wt % to about 30 wt % for the (meth)acrylate monomers, about 2 wt % to about 20 wt % for the nitrocellulose, about 2 to about 30 wt % for the rapid release copolymer, about 5 wt % to about 30 wt % for the dicarbamate oligomer, about 0 wt % to about 10 wt % for the plasticizer, about 0.1 wt % to about 10 wt % for the photoinitiator and about 30 wt % to about 70 wt % for the ethyl acetate.

9. A composition according to statement 8 wherein the weight percentage ranges of the (meth)acrylate monomers relative to the total weight of the composition are about 5.8 wt % to about 6.8 wt % for hydroxypropyl (meth)acrylate; about 2.6 wt % to about 3.2 wt % for hydroxyethyl (meth)

acrylate, about 2.2 wt % to about 2.8 wt % for isobornyl (meth)acrylate and about 0 wt % to about 0.9 wt % for acrylic acid.

10. A composition according to any one of statements 1-9 wherein the nitrocellulose has a low to moderate degree of nitration of the hydroxyls of the beta glucose unit of cellulose.

11. A composition according to statement 10 wherein the weight percent of nitrogen relative to the total weight of the nitrocellulose ranges from about 10 wt % to about 12.3 wt %.

12. A photopolymerized composition comprising a crosslinked (meth)acrylate polymer of multiple (meth)acrylate monomers and di-(hydroxyethylmethacryloyl) trimethylhexyl dicarbamate oligomer of weight average molecular weight in the range of 10 kDa to 20 kDa, which is in a mixture with nitrocellulose, a rapid release copolymer of alkyl acrylate monomers, one or more plasticizers and a photoinitiator.

13. A photopolymerized composition of statement 13 wherein the multiple (meth)acrylate monomers include hydroxyethyl (meth)acrylate, hydroxypropyl (meth)acrylate, isobornyl (meth)acrylate and acrylic acid, tetrahydrofuranyl (meth)acrylate, butyl (meth)acrylate and methyl (meth)acrylate.

14. A photopolymerized composition according to statement 13 wherein the crosslinked polymer, nitrocellulose, rapid release copolymer, plasticizers and photoinitiator are a substantially homogeneous solid mixture.

15. A photopolymerized composition according to statement 12, 13 or 14 wherein weight percentages relative to the total weight of the photopolymerized composition are about 10.0 wt % to 60.0 wt % of the multiple (meth)acrylate monomers, about 10.0 wt % to about 60.0 wt % of the dicarbamate oligomer, about 4 to about 40.0 wt % of the nitrocellulose, about 4.0 wt % to about 60.0 wt % of the rapid release copolymer, about 0.1 wt % to about 20.0 wt % of the plasticizers, and about 0.2 wt % to about 20.0 wt % of the photoinitiator.

16. A photopolymerized composition according to statement any one of statements 12 to 15 wherein the plasticizers include camphor and trimethyl pentanyl diisobutyrate.

17. A composition according to any one of statements 12 to 16 wherein the rapid release copolymer is a copolymer of butyl acrylate and a mixture of C1 to 25 C3 alkyl acrylates.

18. A composition according to statement 17 wherein the rapid release copolymer has a weight average molecular weight range from 3 kDa to 20 kDa.

19. A composition according to statement 17 or 18 wherein the molar ratio of butyl acrylate to the mixture of alkyl acrylates ranges from 0.5:1 to 2:1.

20. A photopolymerized composition according to statement any one of statements 12-19 wherein weight percentage ranges of the (meth)acrylate monomers relative to the total weight of the composition are about 11.6 wt % to about 13.6 wt % for hydroxypropyl (meth)acrylate about 5.2 wt % to about 6.4 wt % for hydroxyethyl (meth)acrylate, about 4.4 wt % to about 5.6 wt % for isobornyl (meth)acrylate and about 0 wt % to about 1.8 wt % for acrylic acid.

21. A photopolymerized composition of any one of statements 12 to 20 wherein the crosslinked poly(meth)acrylate and the nitro cellulose are a substantially homogeneous mixture of polymers.

22. A photopolymerized composition of statement 21 wherein the substantially homogeneous mixture is a substantially homogeneous solid solution.

23. A photopolymerized composition of statement 22 wherein the substantially homogeneous mixture is a substantially homogeneous interpenetrating network of the polymers.

24. A photopolymerized base coat suitable for covering a nail comprising a photopolymerized composition of a crosslinked (meth)acrylate polymer of multiple (meth)acrylate monomers and di-(hydroxyethylmethacryloyl) trimethylhexyl dicarbamate oligomer of weight average molecular weight in the range of 10 kDa to 20 kDa which is in a mixture with nitrocellulose, a rapid release copolymer of alkyl acrylate monomers, one or more plasticizers and a photoinitiator.

25. A photopolymerized base coat according to statement 24 wherein the multiple (meth)acrylate monomers include hydroxyethyl (meth)acrylate, hydroxypropyl (meth)acrylate, isobornyl (meth)acrylate and acrylic acid.

26. A photopolymerized coat according to statement 24 or 25 wherein the crosslinked polymer, nitrocellulose, rapid release copolymer, plasticizers and photoinitiator are a substantially homogeneous solid mixture.

27. A photopolymerized base coat according to statement 24, 25 or 26 wherein weight percentages relative to the total weight of the photopolymerized composition are about 21 wt % to 27 wt % of the multiple (meth)acrylate monomers, about 25 wt % to about 27 wt % of the dicarbamate oligomer, about 19 to about 21 wt % of the nitrocellulose, about 9 wt % to about 11 wt % of the rapid release copolymer, about 9 wt % to about 11 wt % of the plasticizers, and about 5 wt % to about 7 wt % of the photoinitiator.

28. A photopolymerized base coat according to any one of statements 24 to 27 wherein the plasticizers include camphor and trimethyl pentanyl diisobutyrate.

29. A photopolymerized base coat according to any one of statements 24 to 28 wherein the rapid release copolymer is a copolymer of butyl acrylate and a mixture of C1 to C3 alkyl acrylates.

30. A photopolymerized base coat according to statement 29 wherein the rapid release copolymer has a weight average molecular weight range from 3 kDa to 20 kDa.

31. A photopolymerized base coat according to statement 29 or 30 wherein the molar ratio of butyl acrylate to the mixture of alkyl acrylates ranges from 0.5:1 to 2:1.

32. A photopolymerized base coat according to statement any one of statements 24 to 31 wherein weight percentage ranges of the (meth)acrylate monomers relative to the total weight of the composition are about 11.6 wt % to about 13.6 wt % for hydroxypropyl (meth)acrylate; about 5.2 wt % to about 6.4 wt % for hydroxyethyl (meth)acrylate, about 4.4 wt % to about 5.6 wt % for isobornyl (meth)acrylate and about 0 wt % to about 1.8 wt % for acrylic acid.

33. A photopolymerized base coat according to any one of statements 24 to 32 wherein the crosslinked poly(meth)acrylate and the nitro cellulose are a substantially homogeneous mixture of polymers.

34. A photopolymerized base coat according to any one of statements 24 to 33 wherein the photopolymerized coat is a substantially homogeneous mixture.

35. A method for forming a photopolymerized base coat on a nail comprising the steps of:
coating a nail with a photopolymerizable composition of a mixture of multiple (meth)acrylate monomers, nitrocellulose, a rapid release copolymer of alkyl acrylate monomers, a di-(hydroxyethylmethacryloyl) trimethylhexyl dicarbamate oligomer of weight average molecular weight in the range of 13 kDa to 17 kDa, one or more plasticizers and a photoinitiator wherein the mixture is in an ethyl acetate solution, and exposing the photopolymerizable composition with UV radiation for a sufficient time to cure the composition and produce the photopolymerized base coat.

36. A method according to statement 35 wherein the multiple (meth)acrylate monomers include hydroxyethyl (meth)acrylate, hydroxypropyl (meth)acrylate, isobornyl (meth)acrylate and acrylic acid.

37. A method according to statement 36 wherein the plasticizers include camphor and trimethyl pentanyl diisobutyrate.

38. A method according to any one of statements 35, 36 and 37 wherein the rapid release copolymer is a copolymer of butyl acrylate and a mixture of C1 to 25 C3 alkyl acrylates.

39. A method according to statement 38 wherein the rapid release copolymer has a weight average molecular weight range from 3 kDa to 20 kDa.

40. A method according to statement 38 or 39 wherein the molar ratio of butyl acrylate to the mixture of alkyl acrylates ranges from 0.5:1 to 2:1.

41. A method according to any one of statements 35 to 40 wherein the photoinitiator includes a phosphine oxide photoinitiator compound and hydroxycyclohexyl phenyl ketone.

42. A method according to any one of statements 35 to 41 wherein the weight percentage ranges of ingredients relative to the total weight of the photopolymerizable composition are: about 5.0 wt % to about 30.0 wt % for the (meth)acrylate monomers, about 2.0 wt % to about 20.0 wt % for the nitrocellulose, about 2.0 to about 30.0 wt % for the rapid release copolymer, about 5.0 wt % to about 30.0 wt % for the dicarbamate oligomer, about 0.1 wt % to about 10.0 wt % for the plasticizer, about 0.1 wt % to about 10.0 wt % for the photoinitiator and about 30.0 wt % to about 70.0 wt % for the ethyl acetate.

43. A method according to statement 42 wherein the weight percentage ranges of the (meth)acrylate monomers relative to the total weight of the composition are about 5.8 wt % to about 6.8 wt % for hydroxypropyl (meth)acrylate; about 2.6 wt % to about 3.2 wt % for hydroxyethyl (meth)acrylate, about 2.2 wt % to about 2.8 wt % for isobornyl (meth) acrylate and about 0 wt % to about 0.9 wt % for acrylic acid.

44. A method according to any one of statements 35 to 43 wherein the nitrocellulose has a low to moderate degree of nitration of the hydroxyls of the beta glucose unit of cellulose.

45. A method according to statement 44 wherein the weight percent of nitrogen relative to the total weight of the nitrocellulose ranges from about 10 wt % to about 12.3 wt %.

46. A method for removal of a photopolymerized base coat of a crosslinked (meth)acrylate polymer of multiple (meth) acrylate monomers and di-(hydroxyethylmethacryloyl) trimethylhexyl dicarbamate oligomer of weight average molecular weight in the range of 13 kDa to 17 kDa, which is in a mixture with nitrocellulose, a rapid release copolymer of alkyl acrylate monomers, one or more plasticizers and a photoinitiator, comprising: soaking the photopolymerized base coat in an organic solvent to substantially uniformly swell the photopolymerized coat to enable removal of the coat at least as a few large pieces with little or no residual remaining base coat.

47. A method of removal according to statement 46 wherein the organic solvent is acetone, methyl ethyl ketone, isopropanol, ethanol, methyl propyl ketone or any mixture thereof.

48. A method of removal according to statement 46 or 47 wherein the photopolymerized coat swells and is removable in no more than 30 minutes.

49. A method of removal according to any one of statements 46 to 48 wherein the photopolymerized coat is completely swelled and removed and little or no residual particles remain.

50. A method according to statement 49 wherein the swelled photopolymerized coat is removed and no residual particles remain.

51. A photopolymerizable composition, a photopolymerized composition, a photopolymerized base coat, a method for forming and a method for removing according to any one of the preceding claims wherein the preferred (meth)acrylate monomer or monomers and di(meth)acrylate oligomer are methacrylate monomer or monomers and dimethacrylate oligomer.

52. A composition of statement 1, a photopolymerized composition of statement 12 or a photopolymerized base coat of statement 24 wherein the di(meth)acrylate oligomer is di-(hydroxyethylmethacryloyl) trimethylhexyl dicarbamate oligomer chain extended by a chain extension core of a combination of trimethylhexyl diisocyanate and a polyol wherein the diisocyanate is present in a one mole excess relative to the moles of polyol.

53. A composition, photopolymerized composition or photopolymerized base coat of statement 52 wherein the polyol is ethylene glycol, propylene glycol or oligomers thereof.

54. A composition, photopolymerized composition or photopolymerized base coat of statement 53 wherein the polyol is polyethylene glycol containing from 2 to 100 ethylene glycol units.

55. A composition, photopolymerized composition or photopolymerized base coat of statement 53 wherein the polyethylene glycol contains from 20 to 80 ethylene glycol units.

SUMMARY STATEMENTS

The inventions, examples and results described and claimed herein have may attributes and embodiments include, but not limited to, those set forth or described or referenced in this application.

All patents, publications, scientific articles, web sites and other documents and ministerial references or mentioned herein are indicative of the levels of skill of those skilled in the art to which the invention pertains, and each such referenced document and material is hereby incorporated by reference to the same extent as if it had been incorporated verbatim and set forth in its entirety herein. The right is reserved to physically incorporate into this specification any and all materials and information from any such patent, publication, scientific article, web site, electronically available information, text book or other referenced material or document.

The written description of this patent application includes all claims. All claims including all original claims are hereby incorporated by reference in their entirety into the written description portion of the specification and the right is reserved to physically incorporated into the written description or any other portion of the application any and all such claims. Thus, for example, under no circumstances may the patent be interpreted as allegedly not providing a written description for a claim on the assertion that the precise wording of the claim is not set forth in haec verba in written description portion of the patent.

Where features or aspects of the invention are described in terms of Markush groups, those skilled in the art will recognize that the invention is also thereby described in terms of any individual member or subgroup of members of the Markush group. For example, if X is described as selected from the group consisting of methyl, ethyl or propyl, claims for X being methyl and claims for X being methyl and ethyl are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

While the invention has been described in conjunction with the detailed description thereof, the foregoing description is intended to illustrate and not limit the scope of the invention, which is defined by the scope of the appended claims. Thus, from the foregoing, it will be appreciated that, although specific nonlimiting embodiments of the invention have been described herein for the purpose of illustration, various modifications may be made without deviating from the scope of the invention. Other aspects, advantages, and modifications are within the scope of the following claims and the present invention is not limited except as by the appended claims.

What is claimed is:

1. A composition suitable for formation of a photopolymerized base coat on a nail, comprising: a mixture of components including multiple (meth)acrylate monomers comprising hydroxyethyl (meth)acrylate at a weight percentage of about 2 wt % to about 10 wt %, hydroxypropyl (meth)acrylate at a weight percentage of about 5 wt % to about 15 wt %, isobornyl (meth)acrylate at a weight percentage of about 2 wt % to about 4 wt % and acrylic acid at a weight percentage of about 0.1 wt % to about 1 wt % wherein the weight percentage of each of the monomers is relative to the total weight of the composition, nitrocellulose at a nitrogen weight percentage of about 10.7 wt % to about 12.3 wt % relative to the total weight of the nitrocellulose, a rapid release linear copolymer of butyl acrylate and a mixture of methyl and ethyl acrylates wherein the molar ratio of butyl acrylate to the mixture of methyl and ethyl acrylate is in a range of about 1:0.8 to about 1:1.5 and the weight average molecular weight of the rapid release linear copolymer is in a range from about 3 kDa to about 20 kDa, a polyethylene glycol chain extended di-(hydroxyethylmethacryloyl) trimethylhexyl dicarbamate oligomer of weight average molecular weight in the range of 10 kDa to 20 kDa a polydispersity of about 2.0 to about 5.0 and a weight percentage in a range of about 11.0 wt % to about 16 wt % relative to the total weight of the composition, one or more plasticizers and a photoinitiator wherein the mixture is in an ethyl acetate solution.

2. A composition according to claim 1 wherein the one or more plasticizers include camphor and trimethyl pentanyl diisobutyrate.

3. A composition according to claim 1 wherein the rapid release copolymer has a weight average molecular weight range from about 4 kDa to about 10 kDa and has a polydispersity of from about 1.3 to about 2.0.

4. A composition according to claim 1 comprising: about 5 wt % to about 30 wt % of the (meth)acrylate monomers, about 2 wt % to about 20 wt % of the nitrocellulose, about 2 to about 30 wt % of the rapid release copolymer, about 11 wt % to about 16 wt % of the dicarbamate oligomer, about a negligible but detectable wt % to about 10 wt % of the one or more plasticizers, about 0.1 wt % to about 10 wt % of the photoinitiator and about 30 wt % to about 70 wt % of the ethyl acetate.

5. A composition according to claim 1 wherein the weight percentage ranges of the (meth)acrylate monomers comprise about 5.8 wt % to about 6.8 wt % of hydroxypropyl (meth)acrylate; about 2.6 wt % to about 3.2 wt % for of hydroxyethyl (meth)acrylate, about 2.2 wt % to about 2.8 wt % of isobornyl (meth)acrylate and about 0.1 wt % to about 0.9 wt % of acrylic acid.

6. A composition of claim 1 wherein the chain extended oligomer is chain extended by a core formed of polyethylene glycol and trimethylhexyl diisocyanate.

7. A photopolymerized composition comprising a crosslinked (meth)acrylate polymer of multiple (meth)acrylate monomers comprising hydroxyethyl (meth)acrylate, hydroxypropyl (meth)acrylate, isobornyl (meth)acrylate and acrylic acid and which are crosslinked with a polyethylene glycol chain extended di-(hydroxyethylmethacryloyl) trimethylhexyl dicarbamate oligomer of weight average molecular weight in the range of 10 kDa to 20 kDa, a polydispersity of about 2.0 to about 5.0 and wherein the weight percentage of the dicarbamate oligomer is in a range about 22 wt % to about 32 wt % relative to the total weight of the photopolymerized composition, nitrocellulose at a nitrogen weight percentage of about 10.7 wt % to about 12.3 wt % relative to the total weight of the nitrocellulose, a rapid release linear copolymer of, butyl acrylate and a mixture of methyl and ethyl acrylates wherein the molar ratio of butyl acrylate to the methyl and ethyl acrylate mixture is in a range of about 1:0.8 to about 1:1.5 and the weight average molecular weight of the rapid release linear copolymer is in a range from about 3 kDa to about 20 kDa, and one or more plasticizers and a photoinitiator, wherein the nitrocellulose, the crosslinked (meth)acrylate polymer and the rapid release linear copolymer are in a substantially homogeneous single solid phase mixture with each other.

8. A photopolymerized composition of claim 7 wherein the chain extended oligomer is chain extended by a core formed of polyethylene glycol and trimethylhexyl diisocyanate.

9. A photopolymerized base coat suitable for covering a nail comprising a photopolymerized composition of a crosslinked (meth)acrylate polymer of multiple (meth)acrylate monomers comprising hydroxyethyl (meth)acrylate, hydroxypropyl (meth)acrylate, isobornyl (meth)acrylate and acrylic acid which are crosslinked by a polyethylene glycol chain extended di-(hydroxyethylmethacryloyl) trimethylhexyl dicarbamate oligomer of weight average molecular weight in the range of 10 kDa to 20 kDa, a polydispersity of about 2.0 to about 5.0 and a weight percentage of the dicarbamate oligomer in the range of about 22 wt % to about 32 wt % relative to the total weight of the photopolymerized base coat, nitrocellulose at a nitrogen weight percentage of about 10.7 wt % to about 12.3 wt % relative to the total weight of the nitrocellulose, a rapid release linear copolymer of butyl acrylate and a mixture of methyl and ethyl acrylates wherein the molar ratio of butyl acrylate to the mixture of methyl and ethyl acrylate is in a range of about 1:0.8 to about 1:1.5 and the weight average molecular weight of the rapid release linear copolymer is in a range from about 3 kDa to about 20 kDa, and one or more plasticizers and a photoinitiator, wherein the nitrocellulose, the crosslinked (meth) acrylate polymer and the rapid release linear copolymer are in a substantially homogeneous single solid phase mixture with each other.

10. A photopolymerized base coat according to claim 9 wherein the crosslinked polymer, nitrocellulose, rapid release copolymer, one or more plasticizers and photoinitiator are a substantially homogeneous solid mixture.

11. A photopolymerized base coat according to claim 9 comprising about 21 wt % to 27 wt % of the multiple (meth)acrylate monomers, about 25 wt % to about 27 wt % of the dicarbamate oligomer, about 13 to about 15 wt % of the nitrocellulose, about 9 wt % to about 11 wt % of the rapid release copolymer, about 9 wt % to about 11 wt % of the one or more plasticizers, and about 5 wt % to about 7 wt % of the photoinitiator.

* * * * *